United States Patent [19]

Lee et al.

[11] Patent Number: 6,162,950

[45] Date of Patent: Dec. 19, 2000

[54] PREPARATION OF ALKALI METAL TETRAKIS($^F$ARYL)BORATES

[75] Inventors: John Y. Lee; Jamie R. Strickler, both of Baton Rouge, La.

[73] Assignee: Albemarle Corporation, Richmond, Va.

[21] Appl. No.: 09/454,047

[22] Filed: Dec. 3, 1999

[51] Int. Cl.$^7$ .................................................. C07F 5/02
[52] U.S. Cl. ........................................... 568/6; 568/1
[58] Field of Search .............................. 568/1, 6

[56] References Cited

U.S. PATENT DOCUMENTS

| | | | |
|---|---|---|---|
| 5,070,161 | 12/1991 | Nakano et al. | 526/193 |
| 5,078,974 | 1/1992 | Ashby et al. | 422/187 |
| 5,096,936 | 3/1992 | Seko et al. | 522/31 |
| 5,189,222 | 2/1993 | Ashby et al. | 568/1 |
| 5,223,591 | 6/1993 | Nyander et al. | 526/204 |
| 5,340,898 | 8/1994 | Cavezzan et al. | 528/19 |
| 5,399,781 | 3/1995 | Doellein | 568/6 |
| 5,420,355 | 5/1995 | Ikeda et al. | 568/6 |
| 5,468,902 | 11/1995 | Castellanos et al. | 568/6 |
| 5,473,036 | 12/1995 | Piotrowski et al. | 528/4 |
| 5,488,169 | 1/1996 | Ikeda et al. | 568/3 |
| 5,493,056 | 2/1996 | Ikeda et al. | 568/6 |
| 5,510,536 | 4/1996 | Ikeda et al. | 568/6 |
| 5,514,728 | 5/1996 | Lamanna et al. | 522/31 |
| 5,600,003 | 2/1997 | Baur et al. | 568/1 |
| 5,693,867 | 12/1997 | Bauer et al. | 568/1 |
| 5,919,983 | 7/1999 | Rosen et al. | 568/3 |

FOREIGN PATENT DOCUMENTS

| | | |
|---|---|---|
| 0331496 | 9/1989 | European Pat. Off. . |
| 0913400 | 5/1999 | European Pat. Off. . |
| 2727416 | 5/1996 | France . |
| 9295984 | 11/1997 | Japan . |
| 9295985 | 11/1997 | Japan . |
| 9807798 | 2/1998 | WIPO . |
| 9822470 | 5/1998 | WIPO . |

OTHER PUBLICATIONS

Bahr et al., "Trityl Tetrakis(3,5–bis(trifluoromethyl)phenyl)–borate: A New Hydride Abstraction Reagent", J. Org. Chem., 1992, vol. 57, No. 20, pp. 5545–5547.

Brookhart et al., "[(3,5–(CF$_3$)$_2$C$_6$H$_3$)$_4$B]–[H(OEt$_2$)$_2$]: A Convient Reagent for Generation and Stabilization of Cationic, Highly Electrophillic Organometallic Complexes", Organometallics, vol. 11, 1992, pp. 3920–3922.

Chien et al., "Isospecific Polymerization of Propylene Catalyzed by rac–Ethylenebis(indenyl)methylzirconium"Cation"", Journal Am. Chem. Soc. 1991, vol. 113, p. 8570–8571.

Fujiki et al., "Synthesis and Lipophilicities of Tetraarylborate ions substituted with many Trifluoromethyl Groups", Journal of Fluorine Chemistry, vol. 57, 1992, pp. 307–321.

Gol'dberg et al., "Synthesis of Sodium Tetrakis[3,5–DI(Trifluoromethyl)Phenyl]Borate", Zhurnal organicheskoi Khimi, 1989, vol. 25, No. 5, pp. 1099–1102 (translation thereof), pp. 989–991.

Golden et al., "Lithium–Mediated Organofluorine Hydrogen Bonding: Structure of Lithium Tetreakis(3,5–bis(trifluoromethyl)phenyl)borate Tetrahydrate", Inorg. Chem. vol. 33, 1994, pp. 5374–5375.

Hayashi et al., "A Novel Chiral Super–Lewis Acidic Catalyst for Enantioselective Synthesis", J. Am. Chem. Soc., 1996, vol. 118, No. 23, pp. 5502–5503.

Hughes et al., "Synthesis and Structure of the Thallium(I) Salt of the Tetrakis {3,5–bis(trifluoromethyl)phenyl}borate Anion", Inorg. Chem. vol. 36, 1997, pp. 1726–1727.

Jia et al., "Cationic Metallocene Polymerization Catalysts Based on Tetrakis(pentafluorophenyl)borate and Its Derivatives. Probing the Limits of Anion "Noncoordination" via a Synthetic, Solution Dynamic, Structural, and Catalytic Olefin Polymerization Study", Organometallics, 1997, vol. 16, p. 842–857.

Jia et al., "Protected (Fluoroaryl)borates as Effective Counteranions for Cationic Metallocene Polymerization Catalysts", Organometallics, vol. 14, 1995 pp. 3135–3137.

Chem. Abstract #17030, Line H, Myl, et al., "Preparation of Sodium Tetraphenylborate", Benzene Derivatives, 1959, 1 page.

Nesmeyanov et al., "Synthesis of Sodium Tetraphenylboron", Izv. Akad. Nauk SSSR, Otd. Khim. Nauk, 1955, pp. 187. (Translation pp. 167).

Nishida et al., "Tetrakis[3,5–bis(trifluoromethyl)phenyl]borate. Highly Lipophilic Stable Anionic Agent for Solvent–extraction of Cations", Bull Chem. Soc. Jpn., vol. 57, No. 9, 1984, pp. 2600–2604.

Vandeberg et al., "Studies in the Tetraarylborates Part III. The Preparation and Reagent Properties of Sodium Tetrakis(p–Trifluoromethylphenyl) Borate and Sodium Tetrakis(m–Fluorophenyl) Borate", Analytica Chimica Acta, Elsevier Publishing Company, Amsterdam, 1969, vol. 44, pp. 175–183.

Chemical Abstract, # 15921, line G, Vit, Jaroslav, "Preparing Sodium Tetraarylborates, esp. Sodium Tetraphenylborate", Organometallic Compounds, vol. 64, 1966, col. 15921, 1 page.

Chemical Abstract, # 124402W, Wakabayashi et al., "Agrochemical and Industrial Microbicides Containing Tetraphenylborates", 1988, vol. 109, p. 254.

Chemical Abstract, #214696R, Wakabayashi et al., "Pyridinium and Quinolinium Tetraphenylborate Salts as Agrochemical and Industrial Microbicides", Organometallics, 1989, vol. 111, p. 611.

Wittig et al., "Uber Komplexbildung mit Triphenyl–bor (III.Mitt.)", Annalen der Chemie, 1951, vol. 573, pp. 195–209.

(List continued on next page.)

*Primary Examiner*—Jean F Vollano
*Attorney, Agent, or Firm*—Philip M. Pippenger

[57] ABSTRACT

An alkali metal fluoride is reacted with a halomagnesium tetrakis($^F$aryl)borate to form an alkali metal tetrakis($^F$aryl) borate. The alkali metal tetrakis($^F$aryl)borate can be isolated, or the alkali metal cation can be replaced by an organic cation.

49 Claims, No Drawings

OTHER PUBLICATIONS

Chemical Abstract, # 6607, Line D, Wittig et al., "Complex Formation with Triphenylboron. III.", 1951, vol. 46, 1 page.

Chemical Abstract, # 85:86471u, Khol'kin et al., "Synthesis of Metal Tetraphenylborates by the Exchange Extraction Method", Izv. Sib. Otd. Akad. Nauk., 1976, p. 595.

Chemical Abstract, # 125: 196680p, of FR 2,727,416, 1996, p. 20.

Chemical Abstract, # 129: 317638z, of WO 98 46,647, 1998, p. 831.

"Periodic Table of the Elements", Chem. And Eng. News, 1985, pp. 26–27.

PREPARATION OF ALKALI METAL TETRAKIS($^F$ARYL)BORATES

TECHNICAL FIELD

This invention relates to a method for making alkali metal tetrakis($^F$aryl)borates. The alkali metal tetrakis($^F$aryl)borate can be isolated, or the alkali metal cation can be replaced by an organic cation. When the organic cation is a protic ammonium cation or a triarylmethyl cation, the tetrakis ($^F$aryl)borate salt is useful as a polymerization cocatalyst for metallocenes. When the organic cation is an onium cation, the tetrakis($^F$aryl)borate salt is useful as an initiator in crosslinking polyorganosiloxanes.

BACKGROUND

It is known that when a halomagnesium salt of a tetrakis (aryl)borate anion is obtained, reacting the obtained halomagnesium salt with sodium carbonate or sodium bicarbonate yields the corresponding sodium salt of the tetrakis(aryl) borate anion; see Nishida et al., *Bull. Chem. Soc. Jpn.,* 1984, 57, 2600, Fujiki et al., *J. Fluorine Chemistry,* 1992, 57, 307, and EP 913,400. However, the yields of the sodium salt are not always satisfactory; further, Goldberg et al., in *Zhurnal Organicheskoi Khimii,* 1989, 25, 1099, state that the products obtained by Nishida et al. are hydrates. The presence of water in the alkali metal salt of the tetrakis(aryl)borate anion is often undesirable; thus, a process which produces high yields of an alkali metal salt, and especially a dry alkali metal salt, of the tetrakis(aryl)borate anion from the halomagnesium salt is needed.

SUMMARY OF THE INVENTION

This invention provides a method for producing alkali metal tetrakis($^F$aryl)borates in high yield from halomagnesium tetrakis($^F$aryl)borates, independent of the process used to synthesize the halomagnesium salt. Further, the alkali metal salt may be easily dried, and can be isolated. If desired, the alkali metal salt can be reacted, in isolated or non-isolated form, to replace the alkali metal cation with an organic cation.

A first embodiment of this invention is a process which comprises mixing, in a liquid aqueous ethereal reaction medium composed of water and a liquid dihydrocarbyl ether which is substantially immiscible with water in such proportions that a two-phase mixture is obtained, at least one alkali metal fluoride selected from sodium fluoride, potassium fluoride, rubidium fluoride, or cesium fluoride, and a halomagnesium tetrakis($^F$aryl)borate in which each aryl group has bonded directly to an aromatic ring at least two fluorine atoms, or at least two perfluorohydrocarbyl groups, or at least one fluorine atom and at least one perfluorohydrocarbyl group. A solution of an alkali metal tetrakis($^F$aryl) borate in the ethereal phase of a two-phase water/ dihydrocarbyl ether liquid medium is produced.

The borate anion has four fluorine-containing aryl groups, each of which has bonded directly to an aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The $^F$aryl groups may be the same or different from each other; it is preferred that all four $^F$aryl groups are the same.

Another embodiment of this invention is a process which comprises mixing at least a portion of the alkali metal tetrakis($^F$aryl)borate produced in the first embodiment in a liquid medium with a) a protic ammonium salt, b) an onium salt, or c) a triarylmethyl salt, to produce a protic ammonium tetrakis($^F$aryl)borate, an onium tetrakis($^F$aryl)borate, or a triarylmethyl tetrakis($^F$aryl)borate. The protic ammonium cation has the formula [R$_3$NH]$^⊕$, in which each R is independently a hydrocarbyl group containing up to about thirty carbon atoms, and the onium cation has the formula [ER$_n$]$^⊕$, wherein E is an element of any of Groups 15–17 of the Periodic Table, wherein each R is independently a hydrocarbyl group containing up to about thirty carbon atoms, and wherein n is equal to the valence of E plus one. For labeling of the groups of the Periodic Table, see for example, the Periodic Table appearing in *Chemical & Engineering News,* 1985, 69, 26.

Further embodiments of this invention will be apparent from the ensuing description and appended claims.

FURTHER DETAILED DESCRIPTION OF THE INVENTION

For the production of the alkali metal tetrakis($^F$aryl) borate, the liquid aqueous ethereal medium is a mixture comprising water and one or more liquid dihydrocarbyl ethers, particularly those ethers that are substantially immiscible with water, such that a two-phase mixture will be formed. Ethers that may be used include, for example, diethyl ether, di-n-propyl ether, diisopropyl ether, tert-butyl ethyl ether, diheptyl ether, and similar compounds. Preferred ethers are diethyl ether and diisopropyl ether, especially diethyl ether. The proportions of water and ether are such that either component can be present in a larger amount than the other; however, a large excess of either solvent is unnecessary. Preferred ratios of water to ether are in the range of from about 0.2 parts to about three parts by volume of water per part by volume of ether.

The halogen atom of the halomagnesium moiety of the halomagnesium tetrakis($^F$aryl)borate may be a chlorine atom, bromine atom, or iodine atom. Preferred halogen atoms are chlorine and bromine; most preferred is a bromine atom. Thus, the most preferred halomagnesium moiety is a bromomagnesium moiety.

Throughout this document, the term "$^F$aryl group" shall be understood, when not specified, to mean, as described above, a fluorine-containing aryl group, which has bonded directly to an aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The aromatic ring of the $^F$aryl group may be, but is not limited to, benzene, naphthalene, anthracene, biphenyl, phenanthrene, or indene. Benzene is the preferred aromatic moiety. The perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the aryl groups are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl)silyl, tridecylsilyl, and triphenylsilyl. Examples of $^F$aryl groups that may be present on the borate moiety in this invention include 3,5-bis (trifluoromethyl)phenyl, 2,4,6-tris(trifluoromethyl)-phenyl, 4-[tri(isopropyl)silyl]-tetrafluorophenyl, 4-[dimethyl(tert-butyl)silyl]-tetrafluorophenyl,4'-(methoxy)-octafluorobiphenylyl, 2,3-bis(pentafluoroethyl)-naphthyl, 2-(isopropoxy)-hexafluoronaphthyl, 9,10-bis (heptafluoropropyl)-heptafluoroanthryl, 9,10-bis(p-tolyl)-heptafluorophenanthryl, and 1-(trifluoromethyl)-tetrafluoroindenyl. It is preferred that at most two substituents on the ring of the $^F$aryl group are hydrocarbyl, perfluorohydrocarbyl, or alkoxy, while the rest of the substituents are fluorine atoms.

It is highly preferred to have $^F$aryl groups in which all of the substituents are fluorine atoms. Examples of such groups are pentafluorophenyl, 4-nonafluorobiphenylyl, 2-nonafluorobiphenylyl, 1-heptafluoronaphthyl, 2-heptafluoronaphthyl, 7-nonafluoroanthryl, 9-nonafluorophenanthryl, and analogous groups. The most highly preferred perfluoroaryl group is pentafluorophenyl; thus, the most highly preferred borate is tetrakis (pentafluorophenyl)borate.

The alkali metal fluoride may be combined with the reaction mixture in solid form or as a solution; an aqueous solution of the alkali metal fluoride is particularly preferred. An essentially magnesium-free product is preferred; alkali metal salts which yield such a product are alkali metal fluorides, and include potassium fluoride, rubidium fluoride, and cesium fluoride; particularly preferred is potassium fluoride. While the reaction of sodium fluoride with a halomagnesium tetrakis($^F$aryl)borate produces sodium tetrakis($^F$aryl)borate, it is believed to be present as part of an equilibrium mixture, and separation from the coproduced magnesium salts is not easily achieved. Mixtures of alkali metal fluorides can also be used. Examples of mixtures of alkali metal fluorides include sodium fluoride and potassium fluoride, preferably with potassium fluoride predominate, and cesium fluoride and potassium fluoride, again preferably with potassium fluoride predominate.

The amount of alkali metal fluoride needed for the process will vary with the amount of magnesium present. The reaction is believed to be an equilibrium; thus, excess alkali metal fluoride is preferred in order to force the equilibrium to the right. The alkali metal fluoride is preferably present in at least about 1.3 times the molar amount of magnesium present, and more preferably is present in at least about 2.5 times the molar amount of magnesium present. When the halomagnesium salt is from a reaction mixture obtained via a Grignard synthesis, the mixture normally contains other magnesium salts; in such instances, four moles of magnesium are usually present for each mole of borate anion present.

For production of the alkali metal tetrakis($^F$aryl)borate, the components of the mixture are usually at room temperature when mixed together. During the course of the reaction, some heat may be produced, raising the temperature of the reaction mixture. The mixture may be heated, provided that the temperature does not exceed the thermal decomposition temperature of the alkali metal tetrakis($^F$aryl)borate. A preferred contact time for the components of the reaction is in the range of from about ten minutes to about eight hours. More preferably, the contact time is from about fifteen minutes to about six hours. The resultant magnesium salts, including magnesium fluoride, usually migrate to the aqueous phase. The alkali metal tetrakis($^F$aryl)borate is in the ethereal phase, which in the case of the potassium, rubidium, or cesium salt, can easily be separated from the aqueous phase. Removal of the ether from the separated ethereal phase yields solid alkali metal tetrakis($^F$aryl)borate. In the case of the sodium salt, the coproduced magnesium salts remain in the ethereal phase.

Occasionally, the phase boundary in the produced two-phase water/dihydrocarbyl ether mixture is not well defined. Greater amounts of water and/or dihydrocarbyl ether can be used to clarify the phase boundary, but in some instances, it may be necessary to include some hydrocarbon solvent. This hydrocarbon solvent may be included in the water/dihydrocarbyl ether mixture at any time. It is desirable to use enough hydrocarbon solvent to improve the phase boundary without pushing the desired product into the aqueous phase. The amount of hydrocarbon solvent included is preferably in the range of from about 1 wt % to about 50 wt % of the weight of dihydrocarbyl ether. Suitable hydrocarbon solvents include, but are not limited to, pentane, cyclopentane, hexane, cyclohexane, methylcyclohexane, heptane, octane, benzene, toluene, xylenes, and mixtures of hydrocarbon solvents. Particularly preferred as the hydrocarbon solvent is pentane. The inclusion of some hydrocarbon solvent is not usually effective for improving the separation of sodium tetrakis($^F$aryl)borates. Other methods, such as chromatography, may yield good separation of the sodium tetrakis($^F$aryl)borate from the coproduced magnesium salts.

For the contacting of alkali metal tetrakis($^F$aryl)borate and the triarylmethyl salt, the liquid organic solvent may be comprised of one or more liquid hydrocarbons, halogenated hydrocarbons, ethers, or mixtures thereof. Suitable hydrocarbons include linear, branched, and cyclic saturated hydrocarbons, and aromatic hydrocarbons. Examples of suitable hydrocarbons include pentane, hexane, cyclohexane, methylcyclohexane, heptane, cyclooctane, nonane, benzene, toluene, xylene, and the like. Halogenated hydrocarbons that are suitable include dichloromethane, trichloromethane, 1,2-dichloroethane, 1-bromo-2-chloroethane, 1-bromopropane, (chloromethyl) cyclopropane, 1-bromobutane, 1-bromo-2-ethylbutane, 1,1-dichloro-3,3-dimethylbutane, cyclobutyl chloride, neopentyl chloride, 1-bromo-5-chloropentane, cyclopentyl bromide, 1-fluorohexane, 1,6-dibromohexane, trans-1,2-dichlorocyclohexane, 1-chloroheptane, and 1,8-dichlorooctane. Examples of ethers that may be used include diethyl ether, ethyl n-propyl ether, di-n-propyl ether, diisopropyl ether, di-n-butyl ether, tetrahydrofuran, methyltetrahydrofuran, 1,4-dioxane, 1,3-dioxolane, cyclohexylmethyl ether, glyme (the dimethyl ether of ethylene glycol), diglyme (the dimethyl ether of diethylene glycol), triglyme, and tetraglyme. Preferred as the liquid organic solvent are saturated hydrocarbons, particularly those containing up to about ten carbon atoms. Preferably, the liquid organic solvent is dry, and it is preferred that the reaction is conducted in an inert atmosphere comprised of one or more inert gases, such as, for example, nitrogen, helium, or argon.

The term "triarylmethyl cation" refers to carbocations which have three aryl groups bound to a central carbon atom. The aryl groups of the triarylmethyl cation have from six to about twenty carbon atoms, may be the same or different, and can be substituted or unsubstituted. Examples of suitable aryl groups include phenyl, tolyl, xylyl, naphthyl, and 2-ethylnaphthyl; preferred are tolyl and phenyl; most preferred is phenyl. Thus, the most preferred triarylmethyl cation is a triphenylmethyl cation.

Many inorganic anions may be appropriate counterions for a triarylmethyl cation; examples of suitable inorganic anions include chloride, bromide, iodide, tetrafluoroborate, hexafluorophosphate, and the like. Preferred inorganic anions are the halides, especially chloride; thus, the preferred salt is triphenylmethyl chloride.

The alkali metal tetrakis($^F$aryl)borate may be combined with the triarylmethyl salt and the liquid organic solvent in any order. Mixing of alkali metal tetrakis($^F$aryl)borate with the triarylmethyl salt prior to the addition of the liquid organic solvent may cause the formation of a cake. Thus, it is preferred that both the liquid organic solvent and the triarylmethyl salt are present in the reaction vessel before the alkali metal tetrakis($^F$aryl)borate is added.

Protic ammonium salts of the tetrakis(aryl)borate may be formed from the alkali metal salt of the tetrakis($^F$aryl)borate. These ammonium cations have the general formula $[R_3NH]^\oplus$, wherein each R is independently a hydrocarbyl group containing up to about thirty carbon atoms. R is preferably an aliphatic or aromatic hydrocarbyl group; preferred hydrocarbyl groups include methyl and phenyl. Examples of suitable protic ammonium cations include, but are not limited to, trimethylammonium, triethylammonium, cyclohexyl (dimethyl)ammonium, phenyl(dimethyl)ammonium, diphenyl(ethyl)ammonium, and triphenylammonium cations. As described above for the triarylmethyl salt, many inorganic anions may be appropriate counterions for the protic ammonium cation. Again, the halides, especially chloride, are preferred inorganic anions; thus, the preferred salt is generally a protic ammonium chloride.

The protic ammonium salt can be formed shortly before reacting it with the alkali metal tetrakis($^F$aryl)borate; this is accomplished by reacting $R_3N$, wherein R is defined as for the protic ammonium cations, with a protic acid to form the protic ammonium cation. Preferred protic acids include hydrochloric acid, hydrobromic acid, hydroiodic acid, fluoboric acid, and hexafluorophosphoric acid; hydrochloric acid is a particularly preferred protic acid. Preferably, the protic ammonium cation is formed in aqueous solution.

The liquid medium for contacting the protic ammonium salt and alkali metal tetrakis($^F$aryl)borate may be any of a large variety of solvents, so long as they do not interfere with or decompose the desired reaction products. The exclusion of water is not necessary. When water is at least a part of the liquid/solvent mixture, the aqueous portion is preferably provided by the freshly-made protic ammonium salt solution. When ether is at least a part of the liquid/solvent mixture, it may be provided by the alkali metal tetrakis ($^F$aryl)borate solution. In such case, though it is not considered practical to do so, the alkali metal tetrakis($^F$aryl)borate may be isolated from the ethereal phase in which it was made and dissolved in fresh ether.

Other cations, generally referred to as onium cations, can be exchanged with the alkali metal cation to yield the corresponding onium tetrakis($^F$aryl)borate. Onium cations are defined by the formula $[ER_n]^\oplus$, wherein E is an element of any of Groups 15–17 of the Periodic Table, each R is independently a hydrocarbyl group containing up to about thirty carbon atoms, and n is equal to the valence of E plus one. R is preferably an aliphatic or aromatic hydrocarbyl group. As an example of n, when E is sulfur, which has a valence of two, n is three. As described previously for both the triarylmethyl salt and the protic ammonium salts, many inorganic anions may be appropriate counterions for the onium cation. Preferred inorganic anions are the halides, especially chloride; thus, the preferred salt is generally an onium chloride. Standard cation exchange methods can be used; choice(s) of solvent and temperature will vary with the particular system of onium cation and borate chosen. Examples of suitable onium salts include, but are not limited to, diphenyliodonium chloride, tris(p-tolyl)sulfonium bromide, and tetraethylphosphonium chloride.

Generally, the alkali metal tetrakis($^F$aryl)borate and the triarylmethyl salt, protic ammonium salt, or onium salt are mixed together at room temperature. Mixing at room temperature is preferred because the yield of triarylmethyl, protic ammonium, or onium tetrakis($^F$aryl)borate is often much higher than when the mixture is heated. Some heat may be produced during the course of the reaction, raising the temperature of the mixture. The mixture may be heated, provided that the temperature does not exceed the thermal decomposition temperature of the product of the reaction. Heating during contacting of alkali metal tetrakis($^F$aryl) borate and the triarylmethyl, protic ammonium, or onium salt is preferred when a faster reaction rate is desired. Agitation of the reaction mixture is usually necessary for the reaction to proceed.

The contact time for alkali metal tetrakis($^F$aryl)borate and the protic ammonium salt or onium salt is preferably from about fifteen minutes to about eight hours; more preferred is a time in the range of from about forty-five minutes to about six hours. For mixing the alkali metal tetrakis($^F$aryl)borate and the triarylmethyl salt, the contact time at room temperature is preferably in the range of from about two hours to about thirty hours, and more preferably is in the range of from about ten hours to about twenty-four hours. A contact time for alkali metal tetrakis($^F$aryl)borate and the triarylmethyl salt when heating in the range of from about thirty minutes to about twenty hours is preferred; a more preferable range is from about one hour to about fifteen hours; highly preferred is a contact time in the range of from about two hours to about twelve hours.

The following examples are presented for purposes of illustration, and are not intended to impose limitations on the scope of this invention. In Examples 1–5, bromomagnesium tetrakis(pentafluorophenyl)borate was obtained via a Grignard synthesis route.

EXAMPLE 1

2.0 g of KF (34.4 mmol) is dissolved in 20 g of water; 15 g of diethyl ether are added to this solution. 20 g of a 22.7 wt. % solution of $BrMgB(C_6F_5)_4$ (4.54 g, 5.88 mmol) in diethyl ether is added to the KF solution at 25° C. with stirring during fifteen minutes; the resultant mixture is stirred for a while. A two-phase mixture is obtained; the two phases consist of an upper organic layer and a lower aqueous layer. Because the phase boundary is unclear, 6.0 g of n-pentane is added to the mixture, which is then stirred for an hour. A two-phase mixture is again obtained; the lower liquid layer is removed. The K:Mg weight ratio in the organic phase is 1:1, as determined by ICP.

EXAMPLE 2

Example 1 was repeated, except that only 1.0 g of KF is used, and 6.0 g of diethyl ether is used in place of the n-pentane. All of the $[B(C_6F_5)_4]^\ominus$ is in the ether layer, as determined by NMR. The K:Mg weight ratio in the organic layer is 1:3.06, as determined by ICP.

EXAMPLE 3

3.80 g of KF (65.58 mmol) is dissolved in 30 g of water; 7 g of pentane and 30 g of diethyl ether are then added to this solution. 20 g of a 20.8 wt % solution of $BrMgB(C_6F_5)_4$ (4.16 g, 5.31 mmol) in diethyl ether is slowly added to the KF mixture at 25° C. The resultant two-layer mixture is stirred for one hour at 25° C. The lower liquid layer is then removed. The K:Mg weight ratio in the organic phase is 1000:1, as determined by ICP. The organic solvents are removed, and toluene is added to the solid $K[B(C_6F_5)_4]$. The toluene is distilled at 75° C. in a partial vacuum, yielding solid $K[B(C_6F_5)_4]$. The $K[B(C_6F_5)_4]$ is heated in vacuo at 80–100° C. for two hours; the yield of solid $K[B(C_6F_5)_4]$ is 84%. The K:Mg weight ratio in the solid is 1077:1, as determined by ICP.

EXAMPLE 4

2.23 g of NaF (53 mmol) is dissolved in 60.0 g of water; 40 g of diethyl ether is then added to this solution at 25° C. 20.0 g of a 20.77 wt % solution of $BrMgB(C_6F_5)_4$ (4.15 g, 5.3 mmol) in diethyl ether is added to the NaF solution at 25–35° C. during 30 minutes. Initially, two distinct layers are seen, but a rag, and then a gel, is formed in the ethereal layer. A total of 11.45 g of n-pentane is added, followed by water. No clearing of the gel is observed.

EXAMPLE 5

1.9 g of KF (32.8 mmol) is dissolved in 15 g of water; 3.5 g of pentane and 15 g of diethyl ether are then added to this solution. 10.0 g of a 20.77 wt. % solution of $BrMgB(C_6F_5)_4$ (2.08 g, 2.65 mmol) in diethyl ether is added to the KF mixture at 25–35° C., with stirring, during 30 minutes. The resultant two-layer mixture is stirred for another thirty minutes. The lower, gelatinous liquid layer is then removed. The removed lower liquid layer is rinsed with 15 g of diethyl ether; another two-phase mixture is obtained, the layers are separated, and the upper (ethereal) layer is combined with the original upper layer. The $K[B(C_6F_5)_4]$ is in the ethereal layer.

0.388 g (3.18 mmol) of $(C_6H_5)N(CH_3)_2$ and 0.846 g of 16 wt. % aqueous HCl (0.135 g, 3.71 mmol) are mixed, forming $[(C_6H_5)(CH_3)_2NH]Cl$. 1.0 g of $H_2O$ is added to the mixture. The above-prepared ethereal $K[B(C_6F_5)_4]$ is slowly added to the $[(C_6H_5)(CH_3)_2NH]Cl$ mixture with stirring. This mixture is stirred for an hour at 25° C. The ethereal and aqueous phases are then separated, and the ethereal phase is washed twice, each time with 3.0 g of $H_2O$. After the separation of the water washings from the ethereal phase, the diethyl ether is removed at 25–40° C. in a partial vacuum. The resultant white solid is dried in vacuo at 100° C.; 1.7 g are obtained. The yield of $[(C_6H_5)(CH_3)_2NH][B(C_6F_5)_4]$ is 70.5%, and 8.1% $K[B(C_6F_5)_4]$ is still present, as determined by $^1H$ and $^{19}F$ NMR.

EXAMPLE 6

0.121 g (1 mmol) of $(C_6H_5)N(CH_3)_2$ and 1.1 g of HCl (1.1 mmol) as a 1 molar solution in diethyl ether are mixed, forming $[(C_6H_5)(CH_3)_2NH]Cl$. 4.0 g of diethyl ether are added to the mixture. 0.718 g (1.0 mmol) of the $K[B(C_6F_5)_4]$ solid from Example 3 is then added to the mixture at 25° C. during 10 minutes. This mixture is stirred for an additional 30 minutes at 25° C. The mixture is filtered, removing the solid KCl that is produced. The diethyl ether is evaporated via addition of the mixture to 10.0 g of boiling toluene; 6.0 g of toluene are also removed. At 25° C., 5.0 g of hexane is added to cause the $[(C_6H_5)(CH_3)_2NH][B(C_6F_5)_4]$ to precipitate; the toluene/hexane is then decanted. The precipitate is dissolved in $CH_2Cl_2$, and the $CH_2Cl_2$ is then evaporated in a stream of nitrogen, yielding 0.704 g of solid, for an 87% isolated yield of $[(C_6H_5)(CH_3)_2NH][B(C_6F_5)_4]$. The purity of the $[(C_6H_5)(CH_3)_2NH][B(C_6F_5)_4]$ is at least 99%, as determined by $^1H$ and $^{19}F$ NMR.

EXAMPLE 7

0.718 g (1 mmol) of the $KB(C_6F_5)_4$ solid from Example 3 is added to 8.0 g of dry hexanes and stirred under nitrogen at 25° C. 0.42 g (1.5 mmol) of $(C_6H_5)_3CCl$ is added to the $K[B(C_6F_5)_4]$/hexane slurry during five minutes. The solution quickly becomes yellow in color. The mixture is stirred for twenty hours under nitrogen, and then filtered to collect the solid $[(C_6H_5)_3C][B(C_6F_5)_4]$ and KCl. The solid is washed with 4 g of hexane, and then dissolved in 8.0 g of $CH_2Cl_2$. The remaining undissolved solid is washed with 4.0 g of $CH_2Cl_2$; this $CH_2Cl_2$ wash is combined with the dissolved solids $CH_2Cl_2$ solution. The $CH_2Cl_2$ of the combined solution is then evaporated. Hexane is added and then evaporated, yielding 0.87 g of solid $[(C_6H_5)_3C][B(C_6F_5)_4]$, for an isolated yield of 94%. The purity of the isolated solid $[(C_6H_5)_3C][B(C_6F_5)_4]$ is 98%, as determined by $^1H$ and $^{19}F$ NMR.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises mixing in a liquid aqueous ethereal reaction medium composed of water and a liquid dihydrocarbyl ether in such proportions that a two-phase mixture is obtained:
  i) at least one alkali metal fluoride selected from sodium fluoride, potassium fluoride, rubidium fluoride, and cesium fluoride, and
  ii) a halomagnesium tetrakis(aryl)borate, wherein each of the aryl groups is a fluorine-containing aryl group, each of which has bonded directly to an aromatic ring at least two fluorine atoms, or at least two perfluorohydrocarbyl groups, or at least one fluorine atom and at least one perfluorohydrocarbyl group,
to produce a solution of an alkali metal tetrakis(aryl)borate in the ethereal phase of a two-phase water/dihydrocarbyl ether liquid medium.

2. A process according to claim 1 wherein said liquid aqueous ethereal reaction medium is composed of about 0.2 to about 3 parts by volume of water per part by volume of liquid dihydrocarbyl ether.

3. A process according to claim 1 wherein said dihydrocarbyl ether is diethyl ether and wherein i) is potassium fluoride.

4. A process according to claim 1 wherein the halomagnesium moiety is a bromomagnesium moiety.

5. A process according to claim 1 wherein the aromatic ring of said aryl group is a phenyl ring.

6. A process according to claim 1 wherein all of the positions on said aromatic ring(s) of said aryl group are substituted by fluorine atoms.

7. A process according to claim 5 wherein the aryl group is a pentafluorophenyl group.

8. A process according to claim 7 wherein the tetrakis(aryl)borate is tetrakis(pentafluorophenyl)borate.

9. A process according to claim 1 wherein at least a portion of the solution of alkali metal tetrakis(aryl)borate in the ethereal phase is separated from the aqueous phase.

10. A process according to claim 9 wherein said alkali metal tetrakis(aryl)borate is isolated from said solution of alkali metal tetrakis(aryl)borate in the ethereal phase.

11. A process according to claim 9 wherein the dihydrocarbyl ether is diethyl ether and wherein i) is potassium fluoride.

12. A process according to claim 1 wherein said dihydrocarbyl ether is diethyl ether, wherein i) is potassium fluoride, and wherein at least a portion of the solution of alkali metal tetrakis(aryl)borate in the ethereal phase is separated from the aqueous phase.

13. A process according to claim 12 wherein the halomagnesium tetrakis(aryl)borate is bromomagnesium tetrakis(pentafluorophenyl)borate.

14. A process according to claim 1 wherein i) and ii) are at room temperature when mixed together.

15. A process according to claim 1 wherein some hydrocarbon solvent is included in said two-phase water/dihydrocarbyl ether liquid medium.

16. A process according to claim 15 wherein said hydrocarbon solvent is in the range of from about 1 wt % to about 50 wt % of the amount of dihydrocarbyl ether.

17. A process which comprises:
  A) mixing in a liquid aqueous ethereal reaction medium composed of water and a liquid dihydrocarbyl ether in such proportions that a two-phase mixture is obtained:
    i) at least one alkali metal fluoride selected from sodium fluoride, potassium fluoride, rubidium fluoride, and cesium fluoride, and
    ii) a halomagnesium tetrakis(aryl)borate, wherein each of the aryl groups is a fluorine-containing aryl group, each of which has bonded directly to an aromatic ring at least two fluorine atoms, or at least two perfluorohydrocarbyl groups, or at least one fluorine atom and at least one perfluorohydrocarbyl group,
  to produce a solution of an alkali metal tetrakis(aryl)borate in the ethereal phase of a two-phase water/dihydrocarbyl ether liquid medium; and
  B) mixing, in a liquid medium:
    iii) at least a portion of the alkali metal tetrakis(aryl)borate from A), and
    iv) a salt selected from
      a) a protic ammonium salt, wherein the protic ammonium cation has the formula $[R_3NH]^{\oplus}$, in which each R is independently a hydrocarbyl group containing up to about thirty carbon atoms,
      b) an onium salt, wherein the onium cation has the formula $[ER_n]^{\oplus}$, wherein E is an element of any of Groups 15–17 of the Periodic Table, wherein each R is independently a hydrocarbyl group containing up to about thirty carbon atoms, and wherein n is equal to the valence of E plus one, and
      c) a triarylmethyl salt,
  to produce a protic ammonium tetrakis(aryl)borate, an onium tetrakis(aryl)borate, or a triarylmethyl tetrakis(aryl)borate.

18. A process according to claim 17 wherein in A) said liquid aqueous ethereal reaction medium is composed of about 0.2 to about 3 parts by volume of water per part by volume of liquid dihydrocarbyl ether.

19. A process according to claim 17 wherein in A) the dihydrocarbyl ether is diethyl ether and wherein i) is potassium fluoride.

20. A process according to claim 17 wherein in A) the halomagnesium moiety is a bromomagnesium moiety.

21. A process according to claim 17 wherein the aromatic moiety of said aryl group is a phenyl ring.

22. A process according to claim 17 wherein all of the positions on the aryl ring of said aryl group are substituted by fluorine atoms.

23. A process according to claim 21 wherein the aryl group is a pentafluorophenyl group.

24. A process according to claim 23 wherein the tetrakis(aryl)borate is tetrakis(pentafluorophenyl)borate.

25. A process according to claim 17 wherein in A) at least a portion of the solution of alkali metal tetrakis(aryl)borate in the ethereal phase is separated from the aqueous phase.

26. A process according to claim 25 wherein said dihydrocarbyl ether is diethyl ether and wherein i) is potassium fluoride.

27. A process according to claim 25 wherein the alkali metal tetrakis(aryl)borate is isolated from said solution of alkali metal tetrakis(aryl)borate in the ethereal phase.

28. A process according to claim 17 wherein in A) the dihydrocarbyl ether is diethyl ether, wherein i) is potassium fluoride, and wherein at least a portion of the solution of alkali metal tetrakis(aryl)borate in the ethereal phase is separated from the aqueous phase.

29. A process according to claim 28 wherein the halomagnesium tetrakis(aryl)borate is bromomagnesium tetrakis(pentafluorophenyl)borate.

30. A process according to claim 17 wherein in A), i) and ii) are at room temperature when mixed together.

31. A process according to claim 17 wherein in A) some hydrocarbon solvent is included in the two-phase water/dihydrocarbyl ether liquid medium.

32. A process according to claim 31 wherein said hydrocarbon solvent is in the range from about 1 wt % to about 50 wt % of the amount of dihydrocarbyl ether.

33. A process according to claim 17 wherein in B), iv) is a) or b), and wherein the liquid medium comprises water.

34. A process according to claim 17 wherein in B) the liquid medium comprises a liquid dihydrocarbyl ether.

35. A process according to claim 33 wherein in B) the liquid medium further comprises a liquid dihydrocarbyl ether.

36. A process according to claim 17 wherein in B), iv) is a protic ammonium salt.

37. A process according to claim 36 wherein at least one R group is different from the other two R groups.

38. A process according to claim 36 wherein at least one R group is a phenyl group.

39. A process according to claim 38 wherein the protic ammonium cation is a phenyl(dimethyl)ammonium cation.

40. A process according to claim 17 wherein in B), iv) is an onium salt.

41. A process according to claim 40 wherein at least one R group is a phenyl group.

42. A process according to claim 40 wherein all of the R groups are the same.

43. A process according to claim 17 wherein in B), iv) is a triarylmethyl salt.

44. A process according to claim 43 wherein said liquid medium comprises at least one liquid saturated hydrocarbon.

45. A process according to claim 43 wherein said hydrocarbon is an alkane hydrocarbon or mixture of alkane hydrocarbons.

46. A process according to claim 43 wherein all of the R groups are the same.

47. A process according to claim 43 wherein at least one aryl group is a phenyl group.

48. A process according to claim 47 wherein the triarylmethyl cation is a triphenylmethyl cation.

49. A process according to claim 17 wherein in B), iii) and iv) are at room temperature when mixed together.

* * * * *